(12) United States Patent
Dalvi et al.

(10) Patent No.: US 9,364,540 B2
(45) Date of Patent: Jun. 14, 2016

(54) INHALABLE MEDICAMENT

(71) Applicant: Teva Branded Pharmaceutical Products R&D, Inc., Horsham, PA (US)

(72) Inventors: Mukul Dalvi, Miami, FL (US); Libo Wu, Miami, FL (US)

(73) Assignee: Teva Branded Pharmaceutical Products R&D, Inc., Frazer, PA (US)

( * ) Notice: Subject to any disclaimer, the term of this patent is extended or adjusted under 35 U.S.C. 154(b) by 0 days.

(21) Appl. No.: 14/614,842

(22) Filed: Feb. 5, 2015

(65) Prior Publication Data

US 2015/0190510 A1  Jul. 9, 2015

Related U.S. Application Data

(63) Continuation of application No. PCT/US2014/066840, filed on Nov. 21, 2014.

(60) Provisional application No. 61/907,778, filed on Nov. 22, 2013.

(51) Int. Cl.
*A61M 15/00* (2006.01)
*A61M 11/00* (2006.01)
(Continued)

(52) U.S. Cl.
CPC ............... *A61K 47/02* (2013.01); *A61K 9/007* (2013.01); *A61K 9/008* (2013.01); *A61K 9/0078* (2013.01);
(Continued)

(58) Field of Classification Search
CPC ....... A01N 43/48; A01N 43/54; A01N 43/56; A01N 43/60; A01N 43/64; A01N 43/66; A01N 43/707; A01N 43/72; A01N 43/74; A01N 43/80; A61K 31/00; A61K 31/135; A61K 31/137; A61K 31/16; A61K 31/165; A61K 31/167; A61K 31/192; A61K 31/194; A61K 31/341; A61K 31/365; A61K 31/40; A61K 31/4015; A61K 31/4025; A61K 31/403; A61K 31/404; A61K 31/41; A61K 31/415; A61K 31/4155; A61K 31/416; A61K 31/4178;
(Continued)

(56) References Cited

U.S. PATENT DOCUMENTS 5,676,930 A     10/1997  Jager
6,352,152 B1 *  3/2002   Anderson et al. ............. 206/204
(Continued)

FOREIGN PATENT DOCUMENTS

EP    2606891    6/2013
GB    2264238    8/1993
(Continued)

OTHER PUBLICATIONS

International Search Report and Written Opinion for International Application No. PCT/US2014/066840 mailed Feb. 20, 2015.
(Continued)

*Primary Examiner* — Annette Dixon
(74) *Attorney, Agent, or Firm* — RatnerPrestia

(57) ABSTRACT

The present invention provides a solution formulation for inhalation comprising: a liquid phase; an active ingredient containing a carboxylic ester in which the oxygen atom is covalently bound to a quaternary nitrogen-containing heterocycle, dissolved in the liquid phase; and a magnesium or calcium salt, dissolved in the liquid phase. The formulation is particularly suited to pMDIs and nebulizers.

21 Claims, 1 Drawing Sheet

(51) Int. Cl.
   *A61K 47/02* (2006.01)
   *A61K 9/00* (2006.01)
   *A61K 31/46* (2006.01)
   *A61K 47/06* (2006.01)
   *A61K 47/10* (2006.01)

(52) U.S. Cl.
   CPC ............... *A61K 31/46* (2013.01); *A61K 47/06* (2013.01); *A61K 47/10* (2013.01); *A61M 11/00* (2013.01); *A61M 15/009* (2013.01); *A61M 15/0021* (2014.02)

(58) Field of Classification Search
   CPC .......... A61K 31/4184; A61K 31/4192; A61K 31/4196; A61K 31/422; A61K 31/423; A61K 31/4245; A61K 31/425; A61K 31/427; A61K 31/428; A61K 31/433; A61K 31/4427; A61K 31/4439; A61K 34/454; A61K 31/4545; A61K 31/46; A61K 31/4709; A61K 31/496; A61K 31/498; A61K 31/506; A61K 31/5377; A61K 31/55; A61K 31/56; A61K 31/573; A61K 31/58; A61K 31/69; A61K 38/00; A61K 45/00; A61K 45/06; A61K 47/02; A61K 47/06; A61K 47/16; A61K 47/18; A61K 47/183; A61K 47/24; A61K 9/00; A61K 9/0073; A61K 9/0075; A61K 9/008; A61K 9/12; A61K 9/14; A61K 9/5015; A61M 11/00; A61M 15/00; A61M 15/0065; A61M 15/009; A61M 16/20; A61P 11/00; A61P 11/06; A61P 11/14; A61P 21/00; A61P 25/00; A61P 25/04; A61P 29/00; A61P 29/02; A61P 3/00; A61P 3/10; A61P 31/00; A61P 31/04; A61P 31/10; A61P 31/12; A61P 35/00; A61P 37/00; A61P 37/02; A61P 37/04; A61P 37/08; A61P 43/00; A61P 5/00; A61P 5/02; A61P 7/00; A61P 7/02; A61P 9/00; B05D 5/083; B05D 7/00; B65D 75/26; B65D 77/00; B65D 77/003; B65D 81/26; B65D 81/266; B65D 81/267; B65D 81/268; B65D 83/14; B65D 83/38; B65D 83/54; C07D 207/34; C07D 209/14; C07D 231/12; C07D 231/14; C07D 231/38; C07D 231/56; C07D 233/56; C07D 239/00; C07D 239/54; C07D 239/545; C07D 239/553; C07D 239/60; C07D 249/04; C07D 249/08; C07D 257/00; C07D 257/04; C07D 307/00; C07D 307/54; C07D 307/56; C07D 307/68; C07D 333/00; C07D 333/24; C07D 401/00; C07D 401/04; C07D 401/12; C07D 401/14; C07D 403/00; C07D 403/02; C07D 403/10; C07D 403/12; C07D 405/00; C07D 405/12; C07D 409/00; C07D 409/12; C07D 409/14; C07D 413/00; C07D 413/10; C07D 413/12; C07D 417/00; C07D 417/12; C07D 521/00; C07F 5/02; C07F 5/025; C08G 65/007; C08G 65/336; C09D 183/12; C09D 7/12; C23C 16/325; C23C 16/50
   USPC ............. 128/200.14, 200.21, 200.23, 203.12, 128/203.15; 424/184.1, 43, 44, 45, 46, 489, 424/493, 85.1, 85.2, 94.1
   See application file for complete search history.

(56) References Cited

U.S. PATENT DOCUMENTS

| | | | |
|---|---|---|---|
| 6,406,681 B1 * | 6/2002 | Adjei et al. | 424/45 |
| 2003/0149007 A1 | 8/2003 | Chaudry | |
| 2005/0148550 A1 * | 7/2005 | Sundermann et al. | 514/150 |
| 2007/0265326 A1 * | 11/2007 | Biggadike et al. | 514/406 |
| 2009/0263333 A1 * | 10/2009 | Lulla | A61K 9/0075 424/45 |
| 2011/0023876 A1 * | 2/2011 | Vehring et al. | 128/203.15 |
| 2011/0262547 A1 * | 10/2011 | Musa et al. | 424/493 |
| 2014/0109900 A1 * | 4/2014 | Jinks | 128/200.23 |
| 2015/0150787 A1 * | 6/2015 | Lechuga-Ballesteros et al. | 424/45 |

FOREIGN PATENT DOCUMENTS

| | | |
|---|---|---|
| WO | 9209323 | 6/1992 |
| WO | 0193933 | 12/2001 |

OTHER PUBLICATIONS

Entire patent prosecution history of U.S. Appl. No. 14/419,803, filed Feb. 5, 2015, entitled, "An Inhalable Medicament."

International Search Report for International Application No. PCT/US2014/066872 mailed Feb. 20, 2015.

Written Opinion of the International Searching Authority for International Application No. PCT/US2014/066872 mailed Feb. 20, 2015.

* cited by examiner

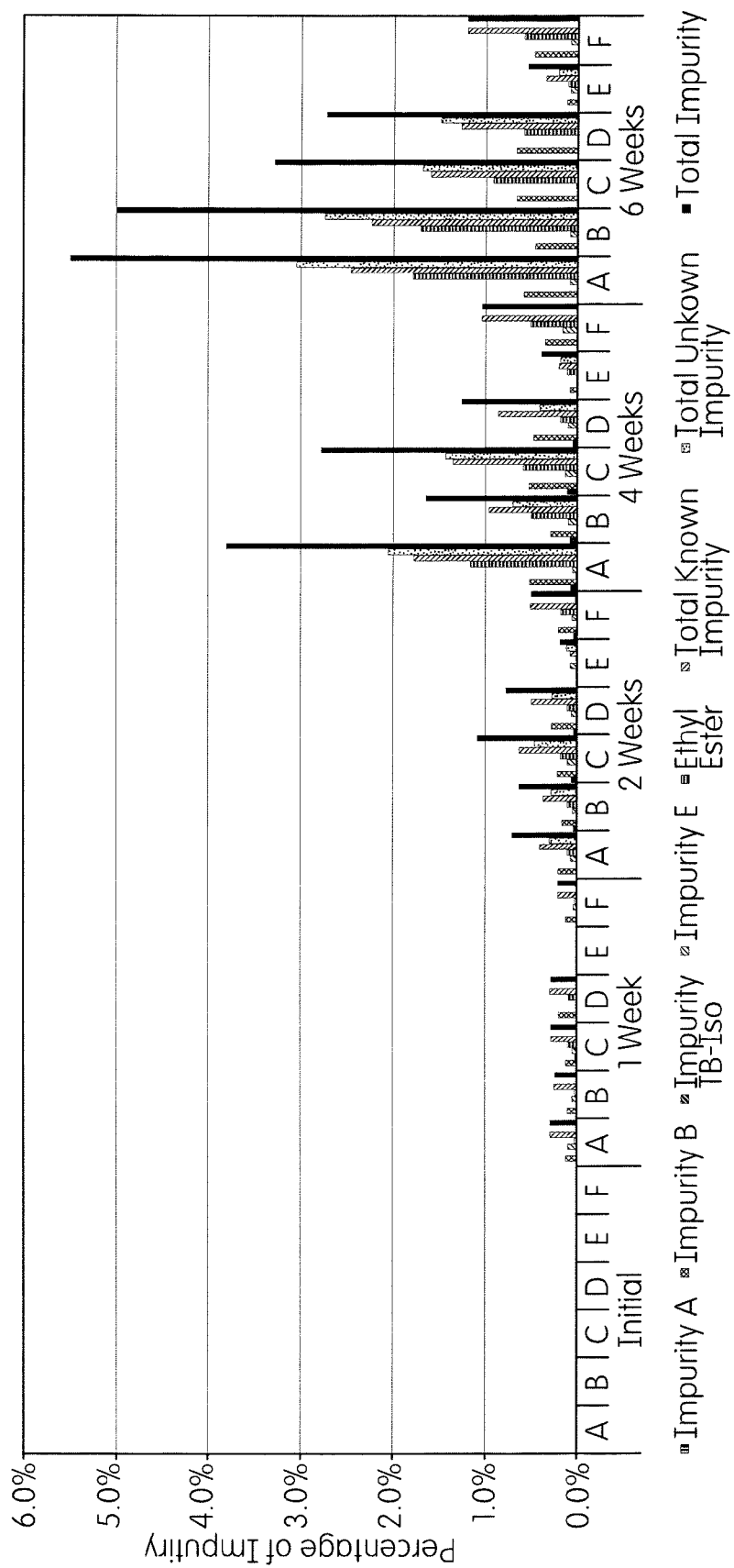

INHALABLE MEDICAMENT

CROSS-REFERENCE TO RELATED APPLICATIONS

This application is a Continuation of International Application No. PCT US2014 066840 filed Nov. 21, 2014, which claims priority to U.S. Provisional Application No. 61/907,778, filed Nov. 22, 2013, the entire disclosure of each of which is incorporated herein by reference for all purposes.

FIELD OF THE INVENTION

The present invention relates to an inhalable medicament and more specifically to a solution formulation comprising an active ingredient susceptible to chemical degradation.

DISCUSSION OF THE RELATED ART

A number of active ingredients commonly used in inhalation therapy and in particular in maintenance bronchodilator treatment to relieve symptoms of patients with asthma and chronic obstructive pulmonary disease (COPD) have structures based around quaternary derivatives of atropine. These active ingredients tend to belong to a class of compounds known as antimuscarinic agents, which are compounds that operate on the muscarinic acetylcholine receptors.

Atropine has the structure:

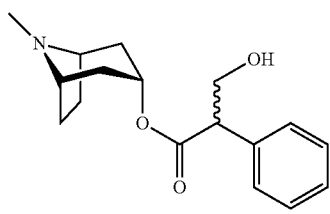

Atropine is based around a carboxylic ester in which the oxygen atom is covalently bound to a nitrogen-containing heterocycle. The quaternary derivatives of atropine which have subsequently been developed contain the carboxylic ester in which the oxygen atom is covalently bound to a quaternary nitrogen-containing heterocycle.

Common examples of active ingredients having this functionality are tiotropium (1), ipratropium (2), glycopyrronium (3), oxitropium (4), aclidinium (5) and trospium (6). The structures of these active ingredients are depicted below, where $X^-$ has been added to denote the counterion.

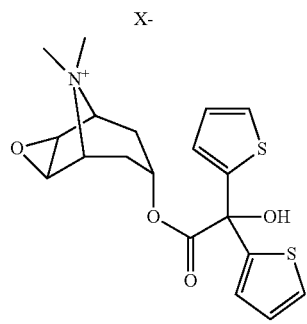

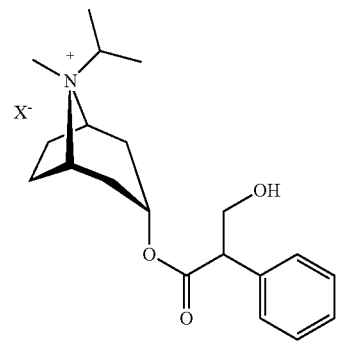

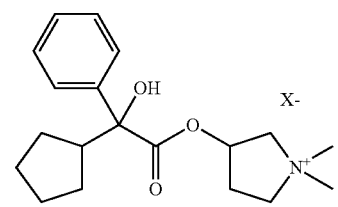

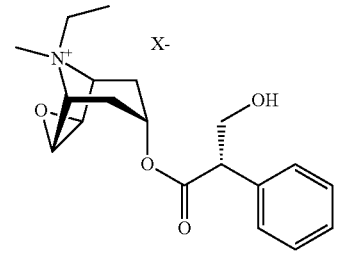

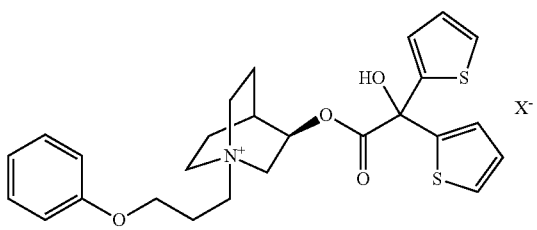

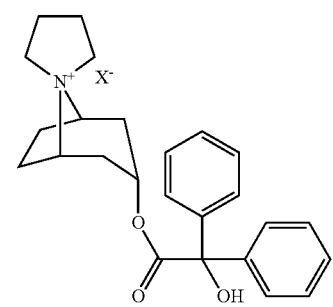

Various approaches have been used for formulating inhalable medicaments, including dry powder inhaler (DPI) formulations, pressurised metered dose inhaler (pMDI) formulations and nebuliser formulations. The purpose of an inhalable formulation is to present the formulation in the form of an aerosol of particles having a particle size suitable for lung deposition (typically a mass median aerodynamic diameter (MMAD) of 1-5 microns). In the case of a liquid formulation, aerosolisation forms droplets of drug dissolved or suspended in the droplets, followed by full or partial evaporation of the liquid phase leading to particles having a size suitable for lung deposition (MMAD as above).

Typically, approaches which use dry powders suffer from the drawback that only a small portion of the powdered active ingredient is actually inhaled into the lungs.

pMDIs and nebulisers are generally more efficient. pMDI and nebuliser formulations may be presented as suspensions or solutions. In a solution formulation, the active ingredient is dissolved in a liquid phase—a hydrofluoroalkane (HFA) propellant for pMDIs or an aqueous phase for nebulisers.

Drawbacks associated with suspensions are potential blockage of the pMDI dispensing nozzle orifice, physical instability of the suspended particles and the requirement to use suspending agents such as surfactants. Solution formulations are easier to manufacture and do not suffer from the above-described drawbacks. However, a significant problem associated with formulating active ingredients as a solution formulation is that active ingredients are chemically more reactive in solution than they are in the solid phase. This is a particular problem for active ingredients containing a carboxylic ester in which the oxygen atom is covalently bound to a quaternary nitrogen-containing heterocycle, because they are particularly sensitive to chemical degradation, particularly hydrolysis or solvolysis of the ester leading to de-esterification and/or trans-esterification (by reaction with any alcohols present in the liquid phase, e.g., ethanol).

Therefore, there remains a need in the art for solution formulations of such active ingredients with increased chemically stability.

SUMMARY OF THE INVENTION

Accordingly, the present invention provides a solution formulation for inhalation comprising:

a liquid phase; an active ingredient containing a carboxylic ester in which the oxygen atom is covalently bound to a quaternary nitrogen-containing heterocycle, dissolved in the liquid phase; and a magnesium or calcium salt, dissolved in the liquid phase.

That is, quaternary derivatives of atropine in solution have been unexpectedly found to be stabilised by dissolved magnesium and calcium salts.

DESCRIPTION OF THE DRAWING

FIG. 1 shows the results of a degradation study using tiotropium bromide.

DETAILED DESCRIPTION OF CERTAIN EMBODIMENTS OF THE INVENTION

The present invention will now be described with reference to the accompanying drawing, in which FIG. 1 shows the results of a degradation study using tiotropium bromide.

The formulation of the present invention contains an active ingredient containing a carboxylic ester in which the oxygen atom is covalently bound to a quaternary nitrogen-containing heterocycle. As previously explained, these active ingredients are conceptually related to atropine, but contain a quaternary nitrogen atom (i.e. a quaternary ammonium cation). The quaternary nitrogen-containing heterocycle is typically saturated. It may be mono-, bi- or tri-cyclic. The active ingredient may also have a hydroxyl group in the α- or β-position with respect to the ester carbonyl carbon atom, more particularly the α-position.

Preferably, the active ingredient is selected from tiotropium, ipratropium, glycopyrronium, oxitropium, aclidinium and trospium. More preferably, the active ingredient is a bromide salt of these active ingredients, e.g., tiotropium bromide.

The amount of the active ingredient present will vary depending on the dose of active ingredient that is required for the particular product, medical indication and patient. Typically, the amount of active ingredient is from 0.001-0.4 wt %, based on the total weight of the formulation and more preferably 0.005-0.1 wt %, based on the total weight of the formulation.

The formulation of the present invention also contains a magnesium or calcium salt. This salt is dissolved in the liquid phase and hence is a soluble salt. The formulation provides a homogeneous phase containing, inter alia, the salt. Preferably, the salt is selected from magnesium chloride, magnesium citrate, calcium chloride and calcium citrate (although magnesium citrate is less preferred for HFA formulations because it is harder to dissolve in such formulations), more preferably from magnesium chloride and calcium chloride, and most preferably, the salt is magnesium chloride. The amount of salt is preferably from 0.0001 to 0.01 wt %, based on the total weight of the formulation. More preferably, the amount of salt is from 0.001 to 0.005 wt %, based on the total weight of the formulation. The salt provides the required stability to the active ingredient when in solution.

The molar ratio of the active ingredient (based on the cation) to salt (based on the magnesium or calcium) is preferably 1:0.5 to 1:3.

Accordingly, the present invention also provides for the use of a magnesium or calcium salt in a solution formulation for inhalation, for the stabilisation of an active ingredient containing a carboxylic ester in which the oxygen atom is covalently bound to a quaternary nitrogen-containing heterocycle.

The formulation of the present invention is a solution formulation and hence the active ingredient, the salt and the liquid phase form a single homogeneous phase. The active ingredient and the salt are dissolved in the liquid phase. Therefore, the active ingredient and the salt must be soluble in the liquid phase. Preferably, the formulation can be cooled to 4° C. and then re-heated to ambient temperature without precipitation of the active ingredient. The present invention does not preclude other components being present in the formulation including components which are not in solution, e.g., other active ingredients which are present in suspended form.

The formulation of the present invention described herein may be a pMDI or a nebuliser formulation. That is, the formulations of the present invention can be used in pMDIs and/or nebulisers.

When the formulation according to the present invention is for a pMDI, the liquid phase comprises an HFA propellant. HFA propellants are well known in the art. The preferred HFAs of the present invention are HFA 134a and/or HFA 227, most preferably HFA 134a.

When the formulation according to the present invention is for a pMDI, the liquid phase may additionally comprise a co-solvent. Suitable examples of co-solvents are water, alcohols having 1 to 3 carbon atoms, alkanes having 3 to 6 carbon atoms and dialkyl ethers having 2 to 4 carbon atoms. Specific examples of suitable co-solvents are water, ethanol, propanol, isopropanol, ethylene glycol, propylene glycol, glycerol, propane, butane, isobutane, pentane, dimethyl ether and diethyl ether.

The co-solvent preferably comprises ethanol, water and/or glycerol. More preferably, the co-solvent comprises ethanol. In a particularly preferred embodiment, the co-solvent comprises ethanol and water. Most preferably, the co-solvent comprises ethanol, water and glycerol.

When the co-solvent comprises ethanol, the ethanol is preferably dehydrated ethanol. The ethanol is principally present to solubilise the active ingredient. In a preferred embodiment, the amount of ethanol is 5 to 25 wt %, more preferably 10 to 20 wt %, based on the total weight to the formulation.

When the co-solvent comprises water, the water is preferably water for inhalation. The water is preferably present at 0.1 to 1.0 wt % and more preferably 0.3 to 0.7 wt %, based on the total weight to the formulation.

When the co-solvent comprises glycerol, the glycerol is present at 0.5 to 2.0 wt %, based on the total weight to the formulation. For some applications, the droplet sizes of the active ingredient dissolved in the liquid phase will be too small for optimal lung deposition. In such cases, glycerol may be added to the formulation. Glycerol is less volatile than most co-solvents used in solution formulations according to the present invention (for example, ethanol) and hence experiences less evaporation on actuation, thereby providing larger droplets (by larger is meant that they have a higher MMAD).

In a preferred embodiment, the formulation comprises tiotropium bromide, ethanol, glycerol, water, citric acid, magnesium chloride and an HFA propellant.

On actuation of a pMDI, a metered dose of the formulation is released from the inhaler. The metered dose of the formulation passes through a valve stem and stem block where it is discharged via an orifice in a dispensing nozzle of the stem block into a mouthpiece and hence to the patient. On release, most of the liquid phase rapidly evaporates The particle size of the emitted particles will depend on a number of factors, including the size of the orifice in the dispensing nozzle, the spray force, the plume geometry, the precise amount of co-solvent used (if present), etc. Typically, however, the particles will be less than 5 microns in diameter (MMAD).

It should be noted that MMADs may be measured using a next-generation impactor (NGI).

pMDIs are well known in the art; see, for example, Drug Delivery to the Respiratory Tract, Eds. D. Ganderton and T. Jones, VCH Publishers, 1987, pages 87-88, or Pharmaceutics—The Science of Dosage Form Design, Second Edition, Ed. M. E. Aulton, Churchill Livingstone, 2002, page 476 et seq for details.

pMDIs typically have a medicament-containing canister and an actuator housing having a mouthpiece. The canister is usually formed from an aluminium cup having a crimped lid which carries a metering valve assembly. The metering valve assembly is provided with a protruding valve stem which is inserted as a push fit into the stem block in the actuator housing.

To actuate, the user applies a compressive force to the closed end of the canister. The internal components of the metering valve assembly are spring loaded so that, typically, a compressive force of 15 to 35 N is required to activate the device. In response to this compressive force, the canister moves axially with respect to the valve stem by an amount varying between about 2 and 4 mm. This degree of axial movement is sufficient to actuate the metering valve and cause a metered quantity of the formulation to be expelled through the valve stem. This is then released into the mouthpiece via an orifice in the dispensing nozzle of the stem block. A user inhaling through the mouthpiece of the device at this point will thus receive a dose of the active ingredient.

An inhalation-actuated inhaler (also known as breath-actuated inhaler) is particularly preferred in order to prevent inadvertent actuation into the eye(s) of the patient. Suitable inhalers are disclosed in WO 92/09323, GB 2 264 238 and WO 01/93933. When the formulation of the present invention is for a pMDI, the present invention most preferably employs the inhaler as described with reference to FIGS. 3-5 of WO 92/09323.

The present invention further provides a pMDI comprising a canister, wherein the canister contains the solution formulation as described herein. The canister is located in the actuator housing as discussed herein. The canister preferably contains 100 actuations or fewer, preferably about 60 actuations (i.e. a one-month supply, based on two actuations per dose). This is a relatively low quantity and hence the head space in the canister tends to be greater than with conventional pMDIs which provides an increased tendency for the active ingredient to degrade chemically. However, even in this more challenging environment, the formulation of the present invention is able to provide the required level of chemical stability. For example, a 10 mL brim-full-capacity canister may have a fill volume of 2.5 to 6.3 mL and a corresponding headspace volume of 7.5 to 3.7 mL. The valve is preferably a 25 to 63 microliter valve, more preferably a 25 or 50 microliter valve.

It has also been found that the formulation of the present invention is not only capable of reducing or preventing chemical degradation of the active ingredient, but also does not significantly affect the material of the canister. This provides the significant advantage that an uncoated aluminium canister may be used, thereby reducing the costs of the pMDI without adversely affecting the formulation. Thus, according to a preferred embodiment of the present invention, the pMDI comprises a canister composed of uncoated aluminium, anodised aluminium (e.g., with hydrofluoric or nitric acid), or aluminium in which the internal surfaces are coated with a fluorinated polymer (e.g., FEP or FCP), more preferably uncoated aluminium.

When the formulation according to the present invention is for a nebuliser, the liquid phase comprises water. Co-solvents may also be present, as described hereinabove with reference to pMDIs.

In a nebuliser, the solution is atomised in order to deliver droplets of the active ingredient in the liquid phase. Nebulisers are well known in the art and further details may be found in, for example, Pharmaceutics—The Science of Dosage form Design" Second Edition, Ed. M. E. Aulton, Churchill Livingston, 2002. Nebulisers include soft-mist generating devices, such as Respimat®.

The formulation of the present invention may additionally comprise citric acid. Citric acid has been found to provide additional stabilisation in the presence of the salts. Preferably, the citric acid is present in 0.01 to 0.2 wt %, based on the total weight of the formulation.

The present invention further provides a nebuliser comprising a reservoir, wherein the reservoir contains the formulation as described herein.

As the formulation is a solution, the formulation does not require the presence of surfactants (which are used to stabilise suspended particles of the active ingredient in a suspension formulation). Accordingly, it is not necessary to add surfactant to the formulation and hence the formulation of the present invention is preferably substantially free of surfactant (e.g., the formulation contains less than 0.0001% by weight of surfactant).

The present invention will now be described with reference to the following example, which is not intended to be limiting.

EXAMPLE

Batches of solution formulations were prepared by combining tiotropium bromide, ethanol, water, glycerol and magnesium chloride (invention) or manganese chloride (comparative) and mixing the components until a solution was formed. All formulations contained 0.015 wt % tiotropium bromide and HFA 134a to 100 wt %. The solution was charged into a canister (as specified in Table 1) which was then sealed with a valve (as specified in Table 1) and filled with HFA 134a. The amounts of the excipients are set out in the Table 1.

TABLE 1

Formulations for degradation studies

Formulation (wt %)

| Batch | Tiotropium bromide | Ethanol | Water | Glycerol | $MnCl_2$ | $MgCl_2$ | Valve | Canister |
|---|---|---|---|---|---|---|---|---|
| A | 0.015 | 20 | 0.5 | 1.5 | 0.0005 | 0 | BK361(RB700) | AA* |
| B | 0.015 | 20 | 0.5 | 1.5 | 0.00025 | 0 | BK361(RB700) | AA* |
| C | 0.015 | 20 | 0.5 | 1.5 | 0 | 0 | BK361(RB700) | AA* |
| D | 0.015 | 20 | 0.5 | 1.5 | 0 | 0 | BK361(RB700) | FEP** |
| E | 0.015 | 20 | 0.5 | 1.5 | 0 | 0.003 | BK361(RB700) | AA* |
| F | 0.015 | 20 | 0.5 | 0 | 0 | 0 | BK357(BK701) | AA* |

*Anodised aluminium
**Fluorinated ethylene propylene

The results of degradation studies conducted at 50° C. are shown in FIG. 1. The impurities left to right within each batch are: known impurity A; known impurity B; known impurity TB-iso; known impurity E; known ethyl ester; total known impurities; total unknown impurities; and total known+unknown impurities. The known impurities are: A 2-hydroxy-2,2-dithiophen-2-ylacetic acid; B (1R,2R,4S,5S,7s)-9-methyl-3-oxa-9-azatricyclo[3.3.1.0$^{2,4}$]nonan-7-yl 2-hydroxy-2,2-dithiophen-2-ylacetate; C (1R,3s,5S)-3-[(2-hydroxy-2,2-dithiophen-2-ylacetyl)oxy]-8,8-dimethyl-8-azoniabicyclo[3.2.1]oct-6-ene bromide; D (1R,3s,5S)-8-methyl-8-azabicyclo[3.2.1]oct-6-en-3-yl 2-hydroxy-2,2-dithiophen-2-ylacetate; E methyl 2-hydroxy-2,2-dithiophen-2-ylacetate; F dithiophen-2-ylmethanone; G (1R,2R,4S,5S,7s)-7-hydroxy-9,9-dimethyl-3-oxa-9-azoniatricyclo[3.3.1.0$^{2,4}$]nonane bromide; H (1s,3RS,4RS,5RS,7SR)-4-hydroxy-6,6-dimethyl-2-oxa-6-azoniatricyclo [3.3.1.0$^{3,7}$]nonane bromide; I (1R,2R,4S,5S,7r)-7-[(2-hydroxy-2,2-dithiophen-2-ylacetyl)oxy]-9,9-dimethyl-3-oxa-9-azoniatricyclo[3.3.1.0$^{2,4}$]nonane bromide; J (1R,3s,5S,8s)-8-(chloromethyl)-3-[(2-hydroxy-2,2-dithiophen-2-ylacetyl)oxy]-8-methyl-8-azoniabicyclo [3.2.1]oct-6-ene chloride; and K (1R,2R,4S,5S,7s)-9-acetyl-3-oxa-9-azatricyclo[3.3.1.0$^{2,4}$]nonan-7-yl 2-hydroxy-2,2-dithiophen-2-ylacetate.

The results show an acceptably low level of chemical degradation after 6 weeks for batch E.

What is claimed is:

1. A solution formulation for inhalation comprising:
   a liquid phase;
   an active ingredient containing a carboxylic ester in which the oxygen atom is covalently bound to a quaternary nitrogen-containing heterocycle, dissolved in the liquid phase; and
   at least one of a magnesium or calcium salt, dissolved in the liquid phase, wherein the amount of salt is from 0.0001 to 0.01 wt %, based on the total weight of the formulation.

2. The formulation as claimed in claim 1, wherein the active ingredient is selected from at least one of tiotropium, ipratropium, glycopyrronium, oxitropium, aclidinium or trospium.

3. The formulation as claimed in claim 1, wherein the active ingredient is tiotropium bromide.

4. The formulation as claimed in claim 1, wherein the salt includes at least one of magnesium chloride, magnesium citrate, calcium chloride or calcium citrate.

5. The formulation as claimed in claim 1, wherein the formulation is for a pressurised metered dose inhaler and the liquid phase comprises an HFA propellant.

6. The formulation as claimed in claim 5, wherein the liquid phase additionally comprises a co-solvent.

7. The formulation as claimed in claim 6, wherein the co-solvent comprises ethanol.

8. The formulation as claimed in claim 7, wherein the formulation comprises tiotropium bromide, ethanol, glycerol, water, citric acid, magnesium chloride and an HFA propellant.

9. The formulation as claimed in claim 1, wherein the formulation is for a nebuliser and the liquid phase comprises water.

10. A metered dose inhaler comprising a canister, wherein the canister contains the formulation as claimed in claim 1.

11. The metered dose inhaler as claimed in claim 10, wherein the canister is composed of aluminium in which the internal surfaces are uncoated.

12. A nebuliser comprising a reservoir, wherein the reservoir contains the formulation as claimed in claim 1.

13. A method of stabilizing an active ingredient containing a carboxylic ester in which the oxygen atom is covalently bound to a quaternary nitrogen-containing heterocycle, wherein the active ingredient is present in a solution formulation for inhalation, the method comprising formulating the solution formulation using at least one of a magnesium salt or a calcium salt in an amount of from 0.0001 to 0.01 wt %, based on the total weight of the formulation.

14. A method of relieving symptoms of a patient with asthma, comprising administering the formulation as claimed in claim 1 to the patient via inhalation.

15. The method of claim 14, wherein the formulation is administered to the patient using a metered dose inhaler comprising a canister and wherein the canister contains the formulation.

16. The method of claim 14, wherein the formulation is administered to the patient using a nebulizer comprising a reservoir and wherein the reservoir contains the formulation.

17. The method of claim 14, wherein the salt includes at least one of magnesium chloride, magnesium citrate, calcium chloride or calcium citrate.

18. A method of relieving symptoms of a patient with chronic obstructive pulmonary disease, comprising administering the formulation as claimed in claim 1 to the patient via inhalation.

19. The method of claim 18, wherein the formulation is administered to the patient using a metered dose inhaler comprising a canister and wherein the canister contains the formulation.

20. The method of claim 18, wherein the formulation is administered to the patient using a nebulizer comprising a reservoir and wherein the reservoir contains the formulation.

21. The method of claim 18, wherein the salt includes at least one of magnesium chloride, magnesium citrate, calcium chloride or calcium citrate.

* * * * *